United States Patent [19]

Niewöhner et al.

[11] Patent Number: 4,868,332
[45] Date of Patent: Sep. 19, 1989

[54] CIRCULATION-ACTIVE NOVEL SUBSTITUTED AMINOMETHYL-5,6,7,8-TETRAHYDRONAPHTHYLOXY-ACETIC ACIDS AND INTERMEDIATES THEREFOR

[75] Inventors: Ulrich Niewöhner, Wermelskirchen; Franz-Peter Hoever, Cologne; Folker Lieb, Leverkusen; Ulrich Rosentreter; Elisabeth Perzborn, both of Wuppertal; Volker-Bernd Fiedler, Leverkusen; Friedel Seuter, Wuppertal, all of Fed. Rep. of Germany

[73] Assignee: Bayer Aktiengesellschaft, Leverkusen, Fed. Rep. of Germany

[21] Appl. No.: 123,748

[22] Filed: Nov. 23, 1987

[30] Foreign Application Priority Data

Dec. 10, 1986 [DE] Fed. Rep. of Germany ....... 3642105

[51] Int. Cl.$^4$ .................. C07C 149/40; C07C 149/41
[52] U.S. Cl. .................................... 562/427; 558/413; 560/10; 564/162
[58] Field of Search ........................ 560/10; 562/427; 564/162; 514/510, 562, 604; 558/413

[56] References Cited

U.S. PATENT DOCUMENTS 3,362,988  1/1988  Bolhofer et al. ..................... 562/462
4,258,058  3/1981  Witte et al. ............................ 560/10

FOREIGN PATENT DOCUMENTS 2362535  6/1974  Fed. Rep. of Germany.

OTHER PUBLICATIONS

Chemical and Pharmaceutical Bulletin, vol. 31, No. 7, Jul., 1983, pp. 2329–2348.
Stout et al., J. Med. Chem., 1982, 25, 326–328.

Primary Examiner—Donald B. Moyer
Assistant Examiner—Julie K. Parker
Attorney, Agent, or Firm—Sprung Horn Kramer & Woods

[57] ABSTRACT

An aminomethyl-5,6,7,8-tetrahydronaphthyl-oxyacetic acid derivative of the formula

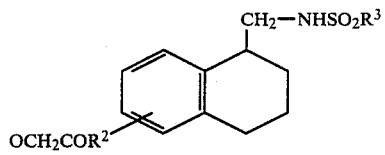

in which
 $R^3$ is aryl or substituted aryl,
 $R^2$ is hydroxyl, alkoxy, phenoxy, benzoxy or $NR^4R^5$, and
 $R^4$ and $R^5$ each independently is hydrogen or alkyl, or one of the radicals $R^4$ or $R^5$ is benzyl, and physiologically acceptable salts thereof with monovalent or divalent cations which have antithrombotic, antiatherosclerotic and antiischaemic activities.

10 Claims, No Drawings

CIRCULATION-ACTIVE NOVEL SUBSTITUTED AMINOMETHYL-5,6,7,8-TETRAHYDRONAPHTHYLOXY-ACETIC ACIDS AND INTERMEDIATES THEREFOR

The present invention relates to new substituted aminomethyl-5,6,7,8-tetrahydronaphthyl-oxyacetic acids, processes for their preparation and their use in medicaments, in particular as antithrombotics, antiathero-sclerotics and antiischaemic agents, and new intermediate products for their preparation.

Thrombosis and arteriosclerotic vascular changes are controlled, above all, by the interaction of two metabolites of arachidonic acid, namely by thromboxan $A_2$ (TXA$_2$) and prostacyclin (PGI$_2$). TXA$_2$ has an aggregating effect on blood platelets, and PGI$_2$ has an antiaggregating effect. Moreover, TXA$_2$ has a vasoconstricting action and PGI$_2$ a vasodilating action.

In a number of thrombo-embolic and ischaemic diseases, hyperaggregability of the platelets or increased platelet consumption leads to increased thromboxan synthesis, so that the TXA$_2$ and PGI$_2$ equilibrium is disturbed. It is therefore desirable in the therapy and prophylaxis of thrombo-embolic and ischaemic diseases for the thromboxan effect to be inhibited and the protective properties of PGI$_2$ thereby to be increased.

It has now been found, surprisingly, that certain substituted aminomethyl-5,6,7,8-tetrahydronaphthyl-oxyacetic acids have a specific and powerful antagonistic action in respect of thromboxan A$_2$.

The invention relates to new substituted amino-methyl-5,6,7,8-tetrahydronaphthyl-oxyacetic acids of the general formula (I)

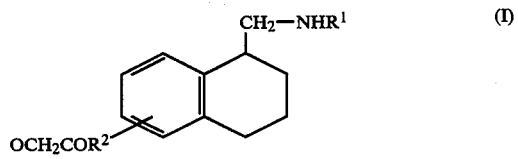

in which
R$^1$ represents SO$_2$R$^3$,
wherein
R$^3$ represents aryl or substituted aryl and
R$^2$ represents hydroxyl, alkoxy, phenoxy, benzoxy or NR$^4$R$^5$,
wherein
R$^4$ and R$^5$ are identical or different and each represent hydrogen or alkyl, or one of the radicals R$^4$ or R$^5$ represents benzyl,
and physiologically acceptable salts thereof with monovalent or divalent cations.

Compounds of the general formula (I) in which
R$^1$ represents SO$_2$R$^3$,
wherein
R$^3$ represents phenyl or naphthyl, which optionally carry 1, 2 or 3 identical or different substituents, such as halogen, cyano, trifluoromethyl and alkyl with 1 to 4 C atoms, and R$^2$ represents hydroxyl, phenoxy, benzoxy or alkoxy with 1 to 4 carbon atoms, or represents the group NR$^4$R$^5$,
wherein
R$^4$ and R$^5$ are identical or different and each represent hydrogen or alkyl with 1 to 4 carbon atoms, or one of the radicals R$^4$ or R$^5$ represents benzyl, and physiologically acceptable salts thereof with monovalent or divalent cations, are of particular interest.

Compounds of the general formula (I) in which R$^3$ represents phenyl which is substituted by fluorine or chlorine are of special interest.

The new substituted aminomethyl-5,6,7,8-tetrahydronaphthalene-oxyacetic acid derivatives of the formula (I) can be both in the form of enantiomers or enantiomer pairs and, if another center of asymmetry exists in one of the radicals, in the form of diastereomer pairs.

It has furthermore been found that the substituted aminomethyl-5,6,7,8-tetrahydronaphthyl-oxyacetic acids of the general formula (I) are obtained by a process in which the amines of the general formula (II)

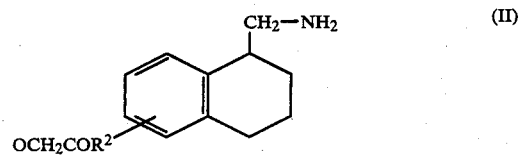

in which
R$^2$ has the abovementioned meaning,
are reacted with sulphonic acids of the general formula R$^3$SO$_3$H,
wherein
R$^3$ has the abovementioned meaning,
or activated derivatives thereof, such as acid chlorides or activated esters, in a manner which is known per se. In the case where R$^2$ ≠ OH, the reaction is followed by hydrolysis to the free carboxylic acids.

The aminomethyltetralin-oxyacetic acid derivatives II are obtained from the corresponding α, β-unsaturated nitriles of the formula III

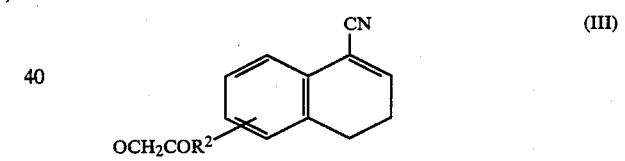

wherein
R$^2$ has the abovementioned meaning,
by catalytic hydrogenation in the presence of NH$_3$. The hydrogenation can preferably be carried out by processes which are known from the literature (see, for example, Rylander, "Catalytic Hydrogenation", Academic Press, Inc., New York, 1967).

The new α,β-unsaturated nitriles III are obtained from tetralones of the formula (IV)

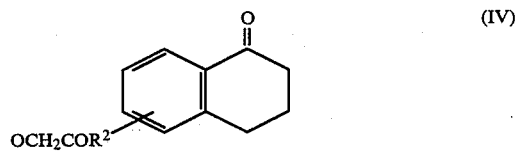

wherein
R$^2$ has the abovementioned meaning,
by reaction with trimethylsilyl cyanide, if appropriate in the presence of a catalyst, the silylated cyanohydrins being formed, and these being reacted directly with acids, such as, for example, hydrogen halide acids, sulfuric acid, nitric acid, trifluoro-acetic acid, methanesulphonic acid or p-toluenesulphonic acid, in suitable protic or aprotic solvents, such as, for example, methanol, ethanol, acetone, tetrahydrofuran, ethyl acetate, toluene, benzene or halogenated solvents, such as methylene chloride, chloroform or carbon tetrachloride, to give the α, β-unsaturated nitriles of the formula III (compare the literature: D. A. Evans, G. L. Carroll, L. H. Truesdale, J. Org. Chem. 39, 914 (1974)).

Instead of trimethylsilyl cyanide, it is also possible to use trimethylsilyl chloride in the presence of an alkali metal cyanide and alkali metal halide in suitable solvents, such as, for example, dimethylformamide or dimethylsulphoxide, by a process analogous to those known from the literature (compare, for example, T. Hiyama, M. Inoue, K. Saito, Synthesis 1986, 645).

The tetralones IV are obtained by alkylation of the corresponding hydroxytetralones V

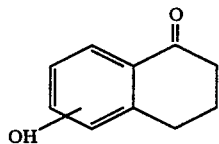
(V)

with acetic acid derivatives of the general formula VI

X—CH$_2$—COR$^2$  (VI)

in which

X denotes a leaving group, such as, for example,

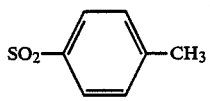

and

R$^2$ has the abovementioned meaning, by processes which are known from the literature (for example Patai "The Chemistry of the Hydroxyl Group", Part 1, pages 454–466, Interscience Publishers, New York, 1971; Tetrahedron 30, 1379 (1974)).

The hydroxytetralones V are known from the literature in some cases (for example J. Org. Chem. 14, page 366 (1949)), and some of them can be prepared by ether cleavage from the known methoxytetralones VII by a process analogous to those known from the literature (for example Org. Syntheses, Vol. 51, page 109; and J. Chem. Soc. 1855 (1949)).

Examples which may be mentioned of the methoxytetralones VII used as starting substances are: 5-methoxy-1-tetralone and 6-methoxy-1-tetralone.

The synthesis sequences can be summarized in an equation as follows, starting from the methoxytetralones VII:

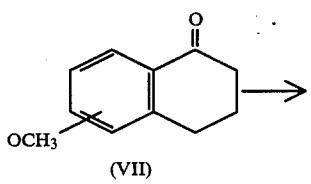
(VII)

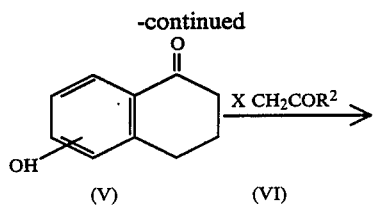
(V)  (VI)

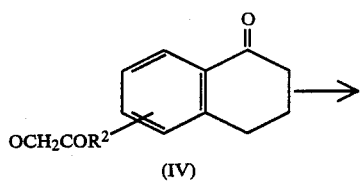
(IV)

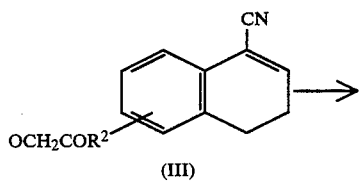
(III)

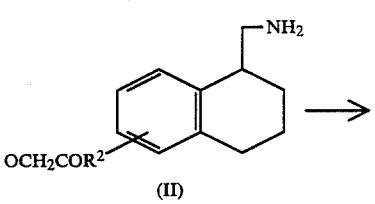
(II)

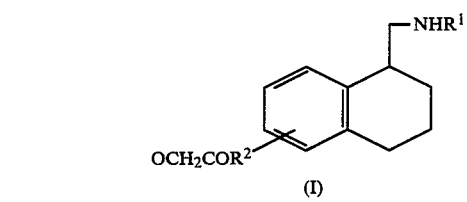
(I)

wherein

R$^1$, R$^2$ and X have the abovementioned meanings.

The end products I are obtained by reacting the amines of the general formula II with the corresponding sulphonic acids R$^3$SO$_3$H or activated derivatives thereof, such as, for example, sulphonic acid chlorides, sulphonic acid anhydrides or sulphonic acid esters, in the presence of an acid-binding agent, such as, for example, alkali metal or alkaline earth metal hydroxides or alkali metal or alkaline earth metal carbonates or organic bases, such as, for example, triethylamine, pyridine or N-ethylmorpholine.

Suitable solvents are, depending on the nature of the sulphonic acid derivative employed, inert organic solvents, such as, for example, methylene chloride, chloroform, ethyl acetate, tetrahydrofuran, ethers, dimethylformamide, pyridine and/or protic solvents, such as, for example, water, methanol and ethanol.

The amines of the general formula II are obtained by catalytic hydrogenation of the α, β-unsaturated nitriles III. Possible catalysts are metals, such as, for example, Raney nickel, palladium or platinum, in the use form known to the expert. Solvents which can be used are protic solvents, such as, for example, methanol and ethanol, and/or aprotic solvents, such as, for example, tetrahydrofuran, toluene, dimethylformamide, methylene chloride or dioxane, to which liquid ammonia is advantageously added. The hydrogenation is carried out under pressures between 5 and 300 atmospheres, advantageously between 50 and 150 atmospheres. The reaction temperature is between 20° and 150° C., advantageously between 30 and 100° C., and the reaction time is 15 minutes to 6 hours.

The α, β-unsaturated nitriles of the general formula III are obtained from the tetralones IV by reaction with trimethylsilyl cyanide. Suitable catalysts for this reaction are Lewis acids, such as, for example, boron trifluoride-etherate, zinc iodide, tin tetrachloride or aluminium trichloride, or organic bases, such as triethylamine, pyridine or the complex of 18-crown-6 and potassium cyanide; the reaction can also be carried out without a catalyst.

The reaction can be carried out in inert organic solvents, such as diethyl ether, tetrahydrofuran, methylene chloride or toluene, or without a solvent.

The reaction temperature is between 0 and 100° C., preferably between 20° and 60° C.

The crude silylated cyanohydrins are converted into the α, β-unsaturated nitriles IV by treatment with an alcoholic hydrogen halide solution. Suitable alcohols are lower aliphatic alcohols, such as, for example, methanol or ethanol, and possible hydrogen halides are hydrogen chloride and hydrogen bromide, preferably hydrogen chloride.

The reaction temperature is between 0° and 50° C., preferably between 0° and 25° C., and the reaction time is between 10 minutes and 6 hours.

Instead of alcoholic hydrogen halide solutions, solutions of other acids, such as, for example, methane-sulphonic acid, p-toluenesulphonic acid or trifluoroacetic acid, in protic or aprotic solvents, such as, for example, benzene or toluene, are suitable.

The tetralins of the general formula IV are obtained by alkylation of the hydroxytetralones of the formula V

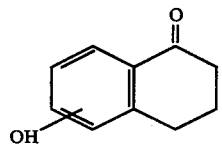 (V)

with acetic acid derivatives of the general formula VI

 (VI)

wherein

X and $R^2$ have the abovementioned meaning.

The alkylation is advantageously carried out in the presence of an acid-binding agent, such as, for example, alkali metal or alkaline earth metal hydroxides or carbonates or organic bases, such as, for example, triethylamine, pyridine or diazabicycloundecane, in organic solvents, such as acetone, butanone, dimethyl-formamide, dimethylsulphoxide, ethanol, dioxane or toluene, or halogenated hydrocarbons, such as methylene chloride or chloroform.

It is often advantageous to add an alkali metal halide, such as, for example, sodium iodide or potassium iodide, and a water-binding agent, such as, for example, molecular sieve 3Å.

The reaction temperature is between 50° and 150°, preferably between 50° and 80° C., depending on the solvent.

Examples which may be mentioned of the compounds of the general formula I are: 5-(4-fluorophenyl-sulphonylaminomethyl)-5,6,7,8-tetrahydro-naphth-1-yl-oxyacetic acid, 5-(3-chlorophenylsulphonylaminomethyl)-5,6,7,8-tetrahydro-naphth-1-yl-oxyacetic acid, 5-(4-methylphenyl- sulphonylaminomethyl)-5,6,7,8-tetrahydro-naphth-1-yl-oxyacetic acid, 5-(4-trifluoromethylphenylsulphonylamino-methyl)-5,6,7,8-tetrahydro-naphth-1-yl-oxyacetic acid, 5-(3,4-dichlorophenylsulphonylaminomethyl)-5,6,7,8-tetra-hydro-naphth-1-yl-oxyacetic acid, 5-(3-chlorophenylsul-phonylaminomethyl)-5,6,7,8-tetrahydro-naphth-2-yl-oxyacetic acid, 5-(4-methylphenylsulphonylaminomethyl)-5,6,7,8-tetrahydro-naphth-2-yl-oxyacetic acid and 5-(4-trifluoromethylphenylsulphonylaminomethyl)-5,6,7,8-tetra-hydro-naphth-2-yl-oxyacetic acid.

Possible formulation forms are the customary galenical administration forms, for example creams, tablets, pills, capsules, suppositories, emulsions and infusion and injection solutions. These formulation forms are prepared by methods which are known per se using customary auxiliaries and excipients.

The medicaments thus prepared are used, for example, by local, parenteral or oral administration, as required.

Formulations which contain the compounds according to the invention in concentrations of about 0.1 to 10% by weight are particularly suitable. Aqueous solutions, which if appropriate are buffered to a pH of 6 to 8, are particularly preferred.

The dosage of the substituted aminomethyl-5,6,7,8-tetrahydro-naphthyl-oxyacetic acid derivatives in the medicaments according to the invention is preferably in a range from 0.05 to 100 mg/kg, in particular 0.1 to 20 mg/kg of body weight.

The substituted aminomethyl-5,6,7,8-tetrahydro-naphthyl-oxyacetic acids contained in the medicaments according to the invention are suitable as thromboxan antagonists and platelet aggregation inhibitors for prevention and treatment of thromboses, thromboembolisms and ischaemic diseases, as antiasthmatics and as antiallergics.

METHOD

Platelet aggregation inhibition in vitro

For the in vitro determination of the platelet aggregation inhibiting action, blood of healthy donors who have not taken any medicament for at least 14 days is used. The blood is taken up in 3.8% strength sodium citrate solution. Platelet-rich plasma (PRP) is obtained by centrifugation at 150 g at room temperature for 20 minutes (Jurgens/Beller: Klinische Methoden der Blutgerinnungsanalyse (Clinical Methods of Blood Coagulation Analysis); Thieme Verlag, Stuttgart 1959). The platelet aggregation is determined by the turbidometric method (Born, G.V.R.: J. Physiol. 162, 67, 1962) in an aggregometer at 37° C. For this, PRP is incubated with the test substance at 37° C. and aggregation is then induced by addition of a collagen suspension. The minimum effective active compound concentration (MEC) which inhibits platelet aggregation in the corresponding PRP samples is stated for the in vitro experiments.

Platelet aggregation inhibition ex vivo

For the ex vivo investigations, the active substance is administered orally in a Tylose suspension to the animals. After 90 minutes, the animals are exsanguinated and the PRP is obtained by means of centrifugation.

The inhibition of aggregation is measured by a method analogous to that described for the in vitro experiments; however, there is no preincubation of the samples.

The results of the collagen-induced platelet aggregation of some examples are shown in the table.

| Example No. | Inhibition of platelet aggregation (in vitro) Limit concentration [mg/l] |
|---|---|
| 9 | 0.3 |
| 10 | 0.3 |
| 15 | 0.01 |
| 16 | 0.1 |
| 17 | 1 |

EXAMPLE 1

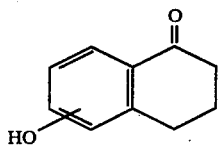

6-Hydroxy-1-tetralone 2 mols of 6-methoxy-1-tetralone are heated at 125° C. in 2 l of 48% strength aqueous hydrobromic acid for 3 hours. On cooling, the product precipitates and is filtered off with suction and dried. If necessary, it can be recrystallized from water.

Yield 86.4% of theory

Melting point: 155° –57° C.

EXAMPLE 2

5-Hydroxy-1-tetralone 1 mol of 5-methoxy-1-tetralone are dissolved in 5 l of methylene chloride and the solution is cooled to −78° C. 500 ml of boron tribromide in 2.3 l of methylene chloride are added dropwise to this solution. The mixture is stirred at −78° C. for 30 minutes and then at 0° C. for 2.5 hours and cooled again to −78° and 3 l of methanol are slowly added dropwise. The mixture is evaporated, the residue is taken up in methylene chloride and the mixture is extracted 3 times with 10% strength sodium hydroxide solution. The combined sodium hydroxide solutions are acidified with concentrated hydrochloric acid and extracted 3 times by shaking with methylene chloride. After drying over sodium sulphate, the extract is evaporated. The residue is pure product and does not need to be recrystallized. The melting point is 210°–215° C.

EXAMPLE 3

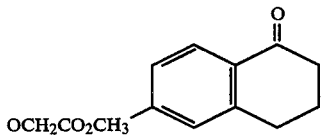

Methyl 5-oxo-5,6,7,8-tetrahydro-naphth-2-yl-oxyacetate 1 mol of 6-hydroxy-1-tetralone, 1.2 mols of methyl chloroacetate, 2 mols of potassium carbonate and 0.1 mol of potassium iodide are boiled under reflux in 2 l of butanone for 6 hours. The mixture is filtered, the residue is rinsed with acetone and the filtrate is evaporated. The residue is taken up in methylene chloride, and the mixture is washed 3 times with 0.5 N NaOH solution, dried over sodium sulphate and evaporated.

Yield: 92% of theory

Melting point: 116° –118° C.

The following compound was prepared in an analogous manner to Example 3:

EXAMPLE 4

Methyl 5-oxo-5,6,7,8-tetrahydro-naphth-1-yl-oxyacetate

Yield: 77% of theory

Melting point: 84°–85° (ligroin)

EXAMPLE 5

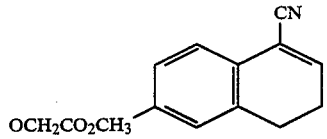

Methyl 5-cyano-7,8-dihydro-naphth-2-yl-oxyacetate 2 to 3 drops of BF₃-etherate solution are added to 0.1 mol of methyl 5-oxo-5,6,7,8-tetrahydro-naphth-2-yl-oxyacetate and 0.15 mol of trimethylsilyl cyanide, and the mixture is stirred at room temperature for 30 minutes and then at 50° C. for 1 hour. 250 ml of a saturated methanolic hydrogen chloride solution are added to this solution at room temperature and the mixture is stirred for 1 hour. Some of the product precipitates out and is filtered off. A further batch is obtained by evaporating the mother liquor, taking up the residue in CH₂Cl₂, extracting the mixture twice by shaking with 0.5N NaOH, drying the extract over Na₂SO₄ and evaporating it and recrystallizing the residue from a little methanol or diisopropyl ether.

Yield: 71% of theory

Melting point: 95° C.

The following compound was prepared analogously to Example 5:

EXAMPLE 6

Methyl 5-cyano-7,8-dihydro-naphth-1-yl-oxyacetate

Yield: 63% of theory

Melting point: 112° C.

EXAMPLE 7

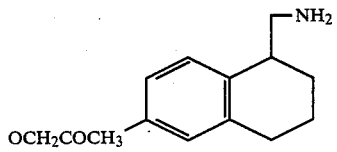

5-Aminomethyl-5,6,7,8-tetrahydro-naphth-2-yl-oxyacetamide 0.25 mol of the αβ-unsaturated nitrile from Example 5 is dissolved in 600 ml of methanol and 185 ml of liquid ammonia. After addition of 22 g of methanol-moist Raney nickel, the mixture is hydrogenated at 70° C. under 100 atmospheres of hydrogen for 3 hours. It is briefly heated under reflux, the catalyst is filtered off hot and the filtrate then evaporated. The product can be further processed directly (see Example 9), or can be precipitated as the hydrochloride from diglyme.

Yield: 96.7% of theory $^1$H-NMR (hydrochloride in CD$_3$OD): δ = 1.75 (m, 4H); 2.78 (m, 2H); 3.1 (m, 2H); 3.15 (m, 1H); 4.45 (s, 2H); 6.8 (m, 2H); 7.17 (m, 1H)

The following compound was prepared analogously to Example 7:

EXAMPLE 8

5-Aminomethyl-5,6,7,8-tetrahydro-naphth-1-yl-oxyacetamide

Yield: 94.2% of theory $^1$H-NMR (hydrochloride in CD$_3$OD): δ = 1.75 (m, 4H); 2.8 (m, 2H); 3.1 (m, 2H); 3.25 (m, 1H); 4.45 (s, 2H); 6.7 to 7.0 (m, 3H)

EXAMPLE 9

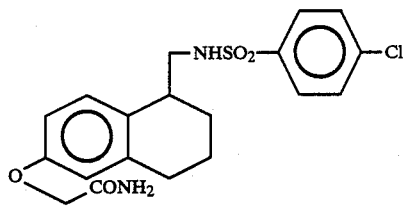

5-(4-Chlorophenylsulphonylaminomethyl)-5,6,7,8-tetra-hydro-naphth-2-yl-oxyacetamide 0.1 mol of 5-aminomethyl-5,6,7,8-tetrahydro-naphth-2-yl-oxyacetamide (Example 7), 0.11 mol of 4-chlorobenzenesulphonyl chloride and 0.11 mol of triethylamine are stirred in 200 ml of tetrahydrofuran at room temperature for 3 hours. The mixture is filtered, the filtrate is evaporated, the residue is taken up in CH$_2$Cl$_2$ and the mixture is washed with 1N HCl, saturated NaHCO$_3$, 1N HCl and saturated NaCl solution, dried over Na$_2$SO$_4$ and evaporated. The residue is purified by flash chromatography over silica gel using CH$_2$Cl$_2$MeOH 5:1.

Yield: 68% of theory $^1$H-NMR (CDCl$_3$): δ = 1.75 (m, 4H); 2.7 (m, 2H); 2.9 (q, 1H); 3.15 (d, 2H); 4.4 (s, 2H); 5.0 (m, 1H); 5.95 (m, 1H); 6.5 (m, 1H); 6.65 (m, 2H); 7.0 (d, 2H); 7.45 (d, 2H); 7.8 (d, 2H)

The following compounds were prepared in an analogous manner to Example 9:

EXAMPLE 10

5-(4-Fluorophenylsulphonylaminomethyl)-5,6,7,8-tetrahydro-naphth-2-yl-oxyacetamide Yield: 77.8% of theory $^1$H-NMR (CD$_3$OD): δ =1.7 (m, 4H); 2.7 (m, 2H); 3.0 (m, 1H); 3.3 (m, 2H); 4.45 (s, 2H); 6.7 (m, 2H); 7.0 (d, 1H); 7.7 to 8.3 (m, 4H)

EXAMPLE 11

5-(3,4-Dichlorophenylsulphonylaminomethyl)-5,6,7,8-tetrahydro-naphth-2-yl-oxyacetamide Yield: 80.2% of theory $^1$H-NMR (CDCl$_3$): δ = 1.7 (m, 4H); 2.7 (m, 2H); 2.9 (q, 1H); 3.15 (m, 2H); 4.4 (1, 2H); 5.2 (m, 1H); 6.0 (m, 1H); 6.6 (m, 1H); 6.65 (m, 2H); 7.0 (d, 1H); 7.3 to 7.9 (m, 3H)

EXAMPLE 12

5-Phenylsulphonylaminomethyl-5,6,7,8-tetrahydro-naphth-2-yl-oxyacetamide

Yield: 73% of theory $^1$H-NMR (CDCl$_3$): δ = 1.75 (m, 4H); 2.7 (m, 2H); 2.95 (q, 1H); 3.1 (m, 12H); 4.4 (s, 2H); 5.2 (m, 1H); 5.95 (m, 1H); 6.6 (m, 1H); 6.65 (m, 2H); 7.0 (d, 1H); 7.4 to 7.7 (m, 3H); 7.8 to 8.05 (m, 2H)

EXAMPLE 13

5-(4-Chlorophenylsulphonylaminomethyl)-5,6,7,8-tetra-hydro-naphth-1-yl-oxyacetamide Yield: 53% of theory m.p. 174° C. (after chromatography, not crystallized)

$^1$H—NMR (CCD$_3$OD): δ = 1.7 (m, 4H); 2.6–3.1(m, 5H); 4.45 (s, 2H); 7 (m. 2H); 7 05 (m, 1); 7 6 (m, 2H ); 7 8 (m, 2H).

EXAMPLE 14

5-Phenylsulphonylaminomethyl-5,6,7,8-tetrahydro-napht--yl-oxyacetamide

Yield: 57% of theory $^1$H-NMR (CDCl3): δ = 1.7 (m, 4H); 2.75 (m, 2H); 2.9 (q, 1H), 3.15 (m, 2H); 4.4 (s, 2H); 5.1 (m, 1H); 6.0 (m, 1H); 6.6 (m, 1H)=; 6.9 (m, 1H); 7.3 (m, 2H); 7.4 to 7.7 (m, 3H); 7.8 to 8.0 (m, 2H)

EXAMPLE 15

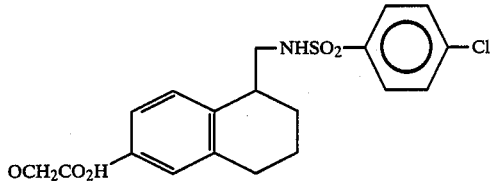

5-(4-Chlorophenylsulphonylaminomethyl)5,6,7,8-tetrahydronaphth-2-yl-oxyacetic acid 0.01 mol of 5-(4-chlorophenylsulphonylaminomethyl)-5,6,7,8-tetrahydro-naphth-2-yl-oxyacetic acid is boiled under reflux with 0.025 mol of KOH in 32 ml of H$_2$O and 100 ml of methanol for 6 hours. The methanol is evaporated off, the aqueous phase is extracted twice by shaking with methylene chloride, and the extract is brought to pH 1 with concentrated hydrochloric acid and extracted twice by shaking with methylene chloride. After the extract has been dried over Na$_2$SO$_4$, it is evaporated, the products being obtained in the pure form as solids.

Yield: 84% of theory

Melting point: 55° to 60° C., foam, not recrystallized

IR (KBr): 1740 cm$^{-1}$ carbonyl band

The following compounds were prepared in an analogous manner to Example 15:

EXAMPLE 16

5-(4-Fluorophenylsulphonylaminometnyl)-5,6,7,8-tetrahydro-naphth-2-yl-oxyacetic acid Yield: 48.5% of theory p IR (KBr): 1740 cm$^{-1}$ carbonyl band

EXAMPLE 17

5-(3,4-Dichlorophenylsulphonylaminomethyl)-5,6,7,8-tetrahydro-naphth-2-yl-oxyacetic acid Yield: 61% of theory
IR (KBr): 1735 cm$^{-1}$ (carbonyl band)

EXAMPLE 18

5-Phenylsulphonylaminomethyl-5,6,7,8-tetrahydronaphth-yl-oxyacetic acid

Yield: 88% of theory
IR (KBr): 1740 cm$^{-1}$ (carbonyl band)

EXAMPLE 19

5-(4-Chlorophenylsulphonylaminomethyl)-5,6,7,8-tetra-hydro-naphth-1-yl-oxyacetic acid Yield: 81% of theory, m.p. 170° C. [foam after chromatography, not IR (KBr): 1735 cm$^{-1}$ (carbonyl band) recrystallized)

EXAMPLE 20

5-Phenylsulphonylaminomethyl-5,6,7,8-tetrahydronapht-yl-oxyacetic acid

Yield: 81% of theory
IR (KBr): 1740 cm $^{-1}$ (carbonyl band)

EXAMPLE 21

5-(4-Fluorophenylsulphonylaminomethyl)-5,6,7,8-tetrahydro-naphth-1-yl-oxyacetic acid Yield: 78% of theory
IR (KBr): 1738 cm $^{-1}$ (carbonyl band) $^1$H-NMR (CD$_3$OD): δ = 1.6–1.95 (m, 4H); 2.55–3.05 (m, 5H); 4.62 (s, 2H); 6.55–6.8 (m, 2H); 7.0 (m, IH); 7.3 (m, 2H); 7.9 (m, 2H) Example 22

5-(4-Fluorophenylsulfonylaminomethyl)-5,6,7,8-tetrahydro-naphth-1-yl-oxyacetamid Yield: 49 % of theory
m.p.: 86° C. (foam after chromatography, notrecrystalised)
$^1$H-NMR (CD$_3$OD): δ = 1.7 (m, 4H); 2.6-3.1 (m, 5H); 4.45 (s, 2H); 6.7 (pseudo-q, 2H); 7.05 (pseudo-t, 1H); 7.3 (m, 2H); 7.9 (m, 2H)

It is understood that the specification and examples are illustrative but not limitative of the present invention and that other embodiments within the spirit and scope of the invention will suggest themselves to those skilled in the art.

We claim:

1. An aminomethyl-5,6,7,8-tetrahydronaphthyl-oxyacetic acid derivative of the formula

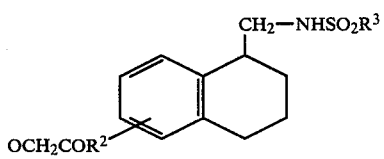

in which
R$^3$ is phenyl or naphthyl, which optionally carries 1 to 3 halogen, cyano, trifluoromethyl or C$_{1-4}$-alkyl substituents,
R$^2$ is hydroxyl, phenoxy, benzoxy, alkoxy with 1 to 4 carbon atoms, or NR$^4$R$^5$, and
R$^4$ and R$^5$ each independently is hydrogen or alkyl with 1 to 4 carbon atoms, or one of the radicals R$^4$ or R$^5$ is benzyl,
or a physiologically acceptable salt thereof with a monovalent or divalent cation.

2. A compound or salt according to claim 1, in which R$^3$ is phenyl which is substituted by fluorine or chlorine.

3. A compound according to claim 1, wherein such compound is 5-(4-chlorophenylsulphonylaminomethyl)-5,6,7,8- tetrahydro-naphth-2-yl-oxyacetic acid of the formula

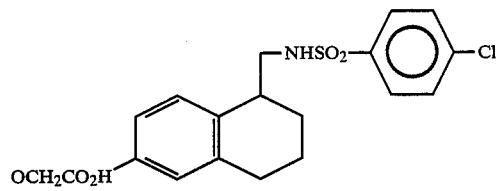

or a physiologically acceptable salt thereof with a monovalent or divalent cation.

4. A compound according to claim 1, wherein such compound is 5-(4-fluorophenylsulphonylaminomethyl)-5,6,7,8-tetrahydro-naphth-2-yl-oxyacetic acid of the formula

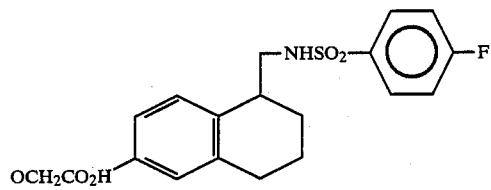

or a physiologically acceptable salt thereof with a monovalent or divalent cation.

5. A compound according to claim 1, wherein such compound is 5-(4-chlorophenylsulphonylaminomethyl)-5,6,7,8-tetrahydro-naphth-!-yl-oxyacetic acid of the formula

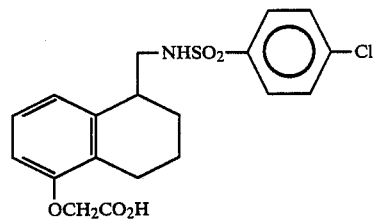

or a physiologically acceptable salt thereof with a monovalent or divalent cation.

6. A compound according to claim 1, wherein such compound is 5-(4-fluorophenylsulphonylaminomethyl)-5,6,7,8-tetrahydro-naphth-1-yl-oxyacetic acid of the formula

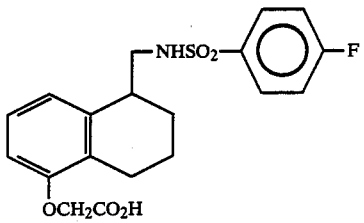

or a physiologically acceptable salt thereof with a monovalent or divalent cation.

7. A composition for inhibiting aggregation of blood platelets comprising an amount effective therefor of a compound or salt according to claim 1 and a pharmacologically acceptable diluent.

8. A unit dose of a compound or salt according to claim 1 in the form of a tablet, ampule or capsule.

9. A method of inhibiting aggregation of blood platelets in a patient in need thereof which comprises administering to such patient an amount effective therefor of a compound or salt according to claim 1.

10. The method according to claim 10, which such compound is 5-(4-chlorophenylsulphonylaminomethyl)-5,6,7,8-tetrahydro-naphth-2-yl-oxyacetic acid, 5-(4-fluorophenylsulphonylaminomethyl)-5,6,7,8-tetrahydro-naphth-2-yl-oxyacetic acid, 5-(4-chlorophenylsulphonylaminomethyl)-5,6,7,8-tetrahydro-naphth-1-yl-oxyacetic acid or 5-(4-fluorophenylsulphonylaminomethyl)-5,6,7,8-tetrahydro-naphth-1-yl-oxyacetic acid, or a physiologically acceptable salt thereof with a monovalent or divalent cation.

* * * * *